United States Patent [19]

Zink et al.

[11] Patent Number: 5,681,791
[45] Date of Patent: Oct. 28, 1997

[54] COLOUR FORMER MIXTURE

[75] Inventors: Rudolf Zink, Therwil, Switzerland; Klaus Huber, Freiburg, Germany

[73] Assignee: Ciba-Geigy Corporation, Tarrytown, N.Y.

[21] Appl. No.: 501,690

[22] Filed: Jul. 12, 1995

Related U.S. Application Data

[63] Continuation-in-part of Ser. No. 312,017, Sep. 26, 1994, abandoned.

[30] Foreign Application Priority Data

Sep. 30, 1993 [CH] Switzerland ............... 2946/93

[51] Int. Cl.$^6$ ............... B41M 5/145; B41M 5/30
[52] U.S. Cl. ............... 503/221; 106/21 R; 428/402.2
[58] Field of Search ............... 427/151; 106/21 R; 503/220, 221, 204

[56] References Cited

U.S. PATENT DOCUMENTS 4,717,423  1/1988  Dyllick-Brenzinge et al. ........... 106/21
5,071,480  12/1991  Zink ........................................... 106/21
5,395,948  3/1995  Zink ............................................ 549/225

FOREIGN PATENT DOCUMENTS 0201225  12/1986  European Pat. Off. ............... 503/220
0561738  9/1993  European Pat. Off. ............... 503/220

Primary Examiner—Bruce H. Hess
Attorney, Agent, or Firm—Kevin T. Mansfield

[57] ABSTRACT

The invention describes a colour former mixture comprising (a) a compound of formula (1) and/or of formula (2) and/or of formula (3) and (b) a compound of formula (4), or a colour former mixture comprising at least two compounds of component (b).

The colour former mixture is suitable for pressure- and particularly for heat-sensitive recording materials and has excellent storage ability and superior paper whiteness.

11 Claims, No Drawings

COLOUR FORMER MIXTURE

This is a continuation-in-part of application Ser. No. 08/312,017 filed on Sep. 26, 1994 now abandoned.

The present invention relates to a colour former mixture and the use thereof in pressure-sensitive and particularly in heat-sensitive recording materials, as well as to novel colour formers and to the preparation of said novel colour formers.

Colour former mixtures which produce strong and stable dyeings in pressure- and heat-sensitive recording systems are disclosed, inter alia, in U.S. Pat. No. 5,071,480.

The object of the present invention is the provision of a colour former mixture, in particular for thermography, which even surpasses the colour former mixtures of the prior art with respect to storage stability and paper whiteness (background).

Specifically, the present invention relates to a colour former mixture comprising (a) a compound of formula

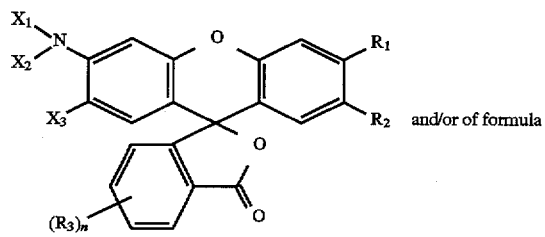

and/or of formula

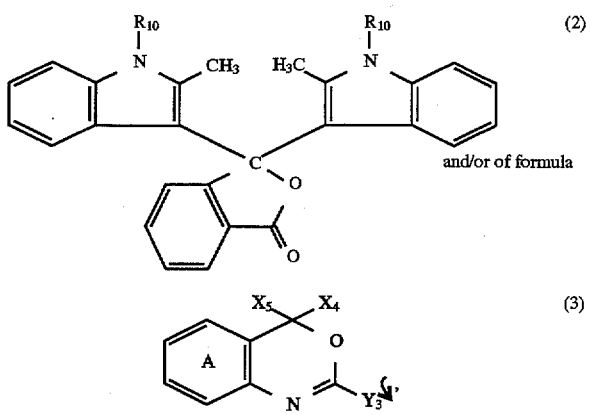

and/or of formula

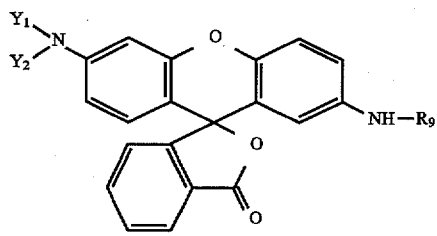

and (b) a compound of formula

(4)

or a colour former system comprising at least two compounds of components (b), wherein $R_1$ is hydrogen, hydroxy, halogen or $C_1$–$C_4$alkyl;

$R_2$ is hydrogen; nitro; $SO_2R_4$; $SO_2OR_5$; $SO_2NR_6R_7$; $COR_8$; $CONR_6R_7$; or $C_1$–$C_4$haloalkyl; phenylamino; phenyl-$C_1$–$C_4$alkylamino; an unsubstituted or halogen- or hydroxy-substituted 2-triazinyl or 1-benzotriazolyl radical;

$R_3$ is halogen; nitro; $C_1$–$C_4$alkyl; $C_1$–$C_4$haloalkyl; amino; mono-$C_1$–$C_4$alkylamino; di-$C_1$–$C_4$alkylamino; or $COR_8$;

$R_4$ is $C_1$–$C_8$alkyl; $C_1$–$C_8$haloalkyl; phenyl or phenyl-$C_1$–$C_4$alkyl, each unsubstituted or substituted in the phenyl moiety by halogen, $C_1$–$C_4$alkyl, $C_1$–$C_4$haloalkyl or $C_1$–$C_4$alkoxy;

$R_5$ is hydrogen; $C_1$–$C_8$alkyl; $C_1$–$C_8$haloalkyl; phenyl or phenyl-$C_1$–$C_4$alkyl, each unsubstituted or substituted in the phenyl moiety by halogen, $C_1$–$C_4$alkyl, $C_1$–$C_4$haloalkyl or $C_1$–$C_4$alkoxy;

$R_6$ and $R_7$ are each independently of the other hydrogen; or $C_1$–$C_8$alkyl; or $R_6$ and $R_7$, together with the linking nitrogen atom, are an unsubstituted or $C_1$–$C_4$alkyl-substituted pyrrolidino, piperidino, morpholino, thiomorpholino or piperazino ring;

$R_8$ is hydrogen; hydroxy; $C_1$–$C_8$alkyl; $C_1$–$C_8$alkoxy; $C_1$–$C_8$haloalkyl; unsubstituted phenyl or phenyl which is substituted by halogen, $C_1$–$C_4$alkyl, $C_1$–$C_4$haloalkyl or $C_1$–$C_4$alkoxy; phenyl-$C_1$–$C_4$alkyl or phenyl-$C_1$–$C_4$alkoxy;

$R_9$ and $R_{10}$ are each independently of the other $C_1$–$C_8$alkyl; or $$-\underset{H}{\overset{|}{C}}=O;$$

$R_{11}$ is hydrogen or $C_1$–$C_5$alkyl;

$R_{12}$ and $R_{13}$ are each independently of the other hydrogen, alkyl or not more than 12 carbon atoms which is unsubstituted or substituted by halogen, hydroxy, cyano or $C_1$–$C_5$alkoxy; $C_5$–$C_7$cycloalkyl, or phenylalkyl or phenyl which is unsubstituted or ring-substituted by halogen, cyano, $C_1$–$C_5$alkyl or $C_1$–$C_5$alkoxy, or $R_{12}$ and $R_{13}$, together with the linking nitrogen atom, are a five- or six-membered heterocyclic radical;

$X_1$ and $X_2$ are each independently of the other hydrogen; $C_1$–$C_8$alkyl; unsubstituted or $C_1$–$C_4$alkyl- or halogen-substituted $C_4$–$C_7$cycloalkyl; unsubstituted phenyl or phenyl which is substituted by $C_1$–$C_4$alkyl, hydroxy or halogen; phenyl-$C_1$–$C_4$alkyl; $C_3$–$C_6$alkenyl; $C_1$–$C_4$alkoxy; $C_1$–$C_4$alkoxy-$C_1$–$C_4$alkyl; 2-tetrahydrofuranyl, or $X_1$ and $X_2$, together with the linking nitrogen atom, are an unsubstituted or $C_1$–$C_4$alkyl-substituted pyrrolidino, piperidino, morpholino, thiomorpholino or piperazino ring;

$X_3$ is hydrogen or $C_1$–$C_4$alkyl;

$X_4$ and $X_5$ are each independently of the other phenyl or phenyl-$C_1$–$C_4$alkyl, each unsubstituted or substituted in the phenyl moiety by halogen, nitro, $C_1$–$C_4$alkyl, $C_1$–$C_4$alkoxy, $C_1$–$C_4$haloalkyl or $-NR_{12}R_{13}$; a 2-pyrrolyl, 2-thienyl, 2- or 3-indolyl, 2-benzofuranyl or 2-naphthothienyl radical;

$Y_1$ and $Y_2$ are each independently of the other $C_1$–$C_5$alkyl;

$Y_3$ is hydrogen; $C_1$–$C_5$alkyl, $C_5$–$C_7$cycloalkyl, unsubstituted phenyl or phenyl which is substituted by halogen, $C_1$–$C_4$alkyl, $C_1$–$C_4$haloalkyl or $C_1$–$C_4$alkoxy;

the benzene ring A may be substituted by halogen; cyano; nitro; $C_1$–$C_5$alkyl; $C_1$–$C_5$alkoxy; $C_1$–$C_5$alkylthio; $C_1$–$C_5$alkylcarbonyl; $C_1$–$C_5$alkoxycarbonyl; or $NR_{12}R_{13}$; and n is 0; 1; 2; 3; or 4.

The components of formulae (1), (2), (3) and (4) may be present as single compounds or as mixtures.

In the literature the individual substituent positions in the fluoran ring are numbered differently. In the present specification, the following numbering has been adopted:

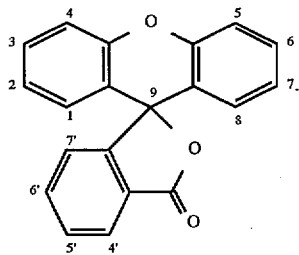

Within the scope of the above definition the respective substituents have the following preferred meanings:

Halogen is fluoro, chloro or bromo, preferably fluoro or chloro.

Within the scope of each definition, alkyl is straight chain or branched alkyl. Illustrative examples of such alkyl groups are methyl, ethyl, n-propyl, isopropyl, n-butyl, 1-methylbutyl, sec-butyl, tert-butyl, n-pentyl, amyl, isoamyl, n-hexyl, 2-ethyl-hexyl, n-heptyl, n-octyl, isooctyl, 1,1,3,3-tetramethylbutyl.

Examples of haloalkyl are preferably the $C_1$–$C_2$haloalkyl radicals, such as trichloromethyl, trifluoromethyl, dichlorofluoromethyl, difluorochloromethyl, perchloroethyl, 1,1,2,2-tetrachloroethyl, 1,1,2,2-tetrafluoroethyl, 2,2,2-trichloroethyl. $R_5$ as $C_1$–$C_8$haloalkyl is preferably haloalkyl as defined above, but also comprises alkyl radicals in which all or at least most of the C—H-bonds are replaced by C—Cl or C—F.

Alkoxy is preferably methoxy, ethoxy, n-propoxy, isopropoxy, n-butoxy, isobutoxy, sec-butoxy and tert-butoxy; $C_1$–$C_4$alkoxy-$C_1$–$C_4$alkyl is preferably methoxymethyl, methoxyethyl, ethoxymethyl or ethoxyethyl.

Mono-$C_1$–$C_5$alkylamino is preferably methylamino, ethylamino, propylamino, butylamino and pentylamino. Di-$C_1$–$C_5$alkylamino comprises both the mixed as well as the corresponding substituted radicals, such as methylethylamino, dimethylamino, diethylamino, methylpropylamino, methylbutylamino, di-n-propylamino, diisopropylamino, di-n-butylamino and di-n-pentylamino and the like.

In phenyl-$C_1$–$C_4$alkyl and phenyl-$C_1$–$C_4$alkoxy, the phenyl moiety may be bound through a straight-chain or branched alkyl or alkoxy chain. Phenethyl, benzyl and phenylmethoxy are preferred.

The phenyl moiety in phenyl-$C_1$–$C_4$alkyl, phenyl-$C_1$–$C_4$alkoxy and phenyl itself is preferably unsubstituted or carries up to three identical or different substituents from among those cited above.

Typical examples of $C_3$–$C_5$alkenyl are allyl, 1-propenyl or 2-pentenyl, isopropenyl or 2-butenyl. Allyl is preferred. $C_4$–$C_7$cyclohexyl is cyclobutyl, cyclopentyl, cyclohexyl or cycloheptyl. Cyclohexyl is preferred.

Of preeminent interest is a colour former mixture comprising (a) a compound of formula

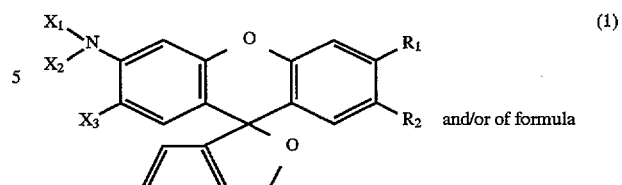

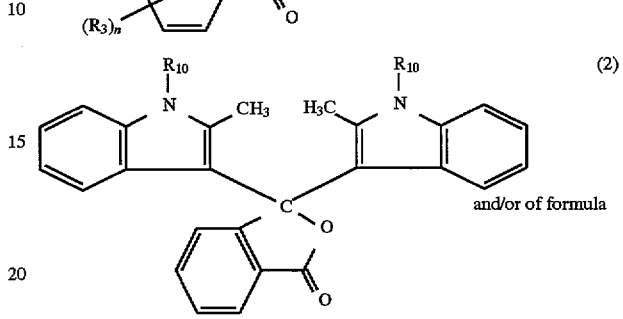

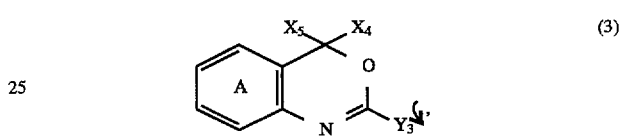

and (b) a compound of formula

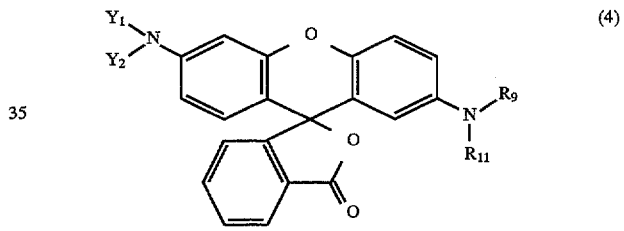

wherein $R_1$ is hydrogen, hydroxy, halogen or $C_1$–$C_4$alkyl;

$R_2$ is hydrogen; nitro; $SO_2R_4$; $SO_2OR_5$; $SO_2NR_6R_7$; $COR_8$; $C_1$–$C_4$haloalkyl; a 2-triazinyl or 1-benzotriazolyl radical which is unsubstituted or substituted by halogen or hydroxy;

$R_3$ is halogen; nitro; $C_1$–$C_4$alkyl; $C_1$–$C_4$haloalkyl; amino; mono-$C_1$–$C_4$alkylamino; di-$C_1$–$C_4$alkylamino; or $COR_8$;

$R_4$ is $C_1$–$C_8$alkyl; $C_1$–$C_8$haloalkyl; phenyl or phenyl-$C_1$–$C_4$alkyl, each unsubstituted or substituted in the phenyl moiety by halogen, $C_1$–$C_4$alkyl, $C_1$–$C_4$haloalkyl or $C_1$–$C_4$alkoxy;

$R_5$ is hydrogen; $C_1$–$C_8$alkyl; $C_1$–$C_8$haloalkyl; phenyl or phenyl-$C_1$–$C_4$alkyl, each unsubstituted or substituted in the phenyl moiety by halogen, $C_1$–$C_4$alkyl, $C_1$–$C_4$haloalkyl or $C_1$–$C_4$alkoxy;

$R_6$ and $R_7$ are each independently of the other hydrogen; or $C_1$–$C_8$alkyl; or $R_6$ and $R_7$, together with the linking nitrogen atom, are an unsubstituted or $C_1$–$C_4$alkyl-substituted pyrrolidino, piperidino, morpholino, thiomorpholino or piperazino ring;

$R_8$ is hydrogen; hydroxy; $C_1$–$C_8$alkyl; $C_1$–$C_8$alkoxy; $C_1$–$C_8$haloalkyl; unsubstituted phenyl or phenyl which is substituted by halogen, $C_1$–$C_4$alkyl, $C_1$–$C_4$haloalkyl, $C_1$–$C_4$alkoxy; phenyl-$C_1$–$C_4$alkyl or phenyl-$C_1$–$C_4$alkoxy;

$R_9$ and $R_{10}$ are each independently of the other $C_1$–$C_8$alkyl; or

$R_{11}$ is hydrogen or $C_1$–$C_5$alkyl;

$R_{12}$ and $R_{13}$ are each independently of the other hydrogen, alkyl of at the most 12 carbon atoms which is unsubstituted or substituted by halogen, hydroxy, cyano or $C_1$–$C_5$alkoxy; $C_5$–$C_7$cycloalkyl, or phenylalkyl or phenyl which is unsubstituted or ring-substituted by halogen, cyano, $C_1$–$C_5$alkyl or $C_1$–$C_5$alkoxy; or $R_{12}$ and $R_{13}$, together with the linking nitrogen atom, are a five- or six-membered heterocyclic radical;

$X_1$ and $X_2$ are each independently of the other hydrogen; $C_1$–$C_4$alkyl; $C_4$–$C_7$cycloalkyl which is unsubstituted or substituted by $C_1$–$C_4$alkyl or halogen; unsubstituted phenyl or phenyl which is substituted by $C_1$–$C_4$alkyl, hydroxy or halogen; phenyl-$C_1$–$C_4$alkyl; $C_3$–$C_6$alkenyl; $C_1$–$C_4$alkoxy; $C_1$–$C_4$alkoxy-$C_1$–$C_4$alkyl; 2-tetrahydrofuranyl, or $X_1$ and $X_2$, together with the linking nitrogen atom, are an unsubstituted or $C_1$–$C_4$alkyl-substituted pyrrolidino, piperidino, morpholino, thiomorpholino or piperazino ring;

$X_3$ is hydrogen or $C_1$–$C_4$alkyl;

$X_4$ and $X_5$ are each independently of the other phenyl or phenyl-$C_1$–$C_4$alkyl, each unsubstituted or substituted in the phenyl moiety by halogen, nitro, $C_1$–$C_4$alkyl, $C_1$–$C_4$alkoxy, $C_1$–$C_4$haloalkyl or —$NR_{12}R_{13}$; a 2-pyrrolyl, 2-thienyl, 2- or 3-indolyl, 2-benzofuranyl or 2-naphthothienyl radical;

$Y_1$ and $Y_2$ are each independently of the other $C_1$–$C_5$alkyl;

$Y_3$ is hydrogen; $C_1$–$C_5$alkyl; $C_5$—$C_7$cycloalkyl, unsubstituted phenyl or phenyl which is substituted by halogen, $C_1$–$C_4$alkyl, $C_1$–$C_4$haloalkyl or $C_1$–$C_4$alkoxy;

the benzene ring A may be substituted by halogen; cyano; nitro; $C_1$–$C_5$alkyl; $C_1$–$C_5$alkoxy; $C_1$–$C_5$alkylthio; $C_1$–$C_5$alkylcarbonyl; $C_1$–$C_5$alkoxycarbonyl; or $NR_{12}R_{13}$; and n is 0; 1; 2; 3; or 4.

In component (a) it is preferred to use colour formers of formula (1), wherein $R_1$ is hydrogen, halogen or $C_1$–$C_4$alkyl;

$R_2$ is nitro; $SO_2R_4$; $SO_2OR_5$; $SO_2NR_6R_7$; $COR_8$; $CONR_6R_7$; or $C_1$–$C_4$haloalkyl;

n is 0, 1, 2, 3 or 4;

$R_3$ if n=1, 2, 3 or 4, is halogen; if n=1 or 2, is $C_1$–$C_4$alkyl or $C_1$–$C_4$haloalkyl; or if n=1, is nitro, $COR_8$, amino, mono-$C_1$–$C_4$alkylamino or di-$C_1$–$C_4$alkylamino;

$R_4$ is $C_1$–$C_4$alkyl; $C_1$–$C_4$haloalkyl; phenyl or phenyl-$C_1$–$C_2$alkyl, each unsubstituted or substituted in the phenyl moiety by halogen, $C_1$–$C_4$alkyl, $C_1$–$C_4$haloalkyl or $C_1$–$C_4$alkoxy;

$R_5$ is hydrogen; $C_1$–$C_4$alkyl; $C_1$–$C_4$haloalkyl; phenyl or phenyl-$C_1$–$C_2$alkyl, each unsubstituted or substituted in the phenyl moiety by halogen, $C_1$–$C_4$alkyl, $C_1$–$C_4$haloalkyl or $C_1$–$C_4$alkoxy;

$R_6$ and $R_7$ are each independently of the other hydrogen; or $C_1$–$C_4$-alkyl; or $R_6$ and $R_7$, together with the linking nitrogen atom, are an unsubstituted or $C_1$–$C_4$alkyl-substituted pyrrolidino or piperidino ring;

$R_8$ is hydrogen; $C_1$–$C_4$alkyl; $C_1$–$C_4$haloalkyl; $C_1$–$C_4$alkoxy; unsubstituted phenyl or phenyl which is substituted by halogen, $C_1$–$C_4$alkyl, $C_1$–$C_4$haloalkyl, $C_1$–$C_4$alkoxy; phenyl-$C_1$–$C_2$alkyl or phenyl-$C_1$–$C_2$alkoxy;

$R_9$ and $R_{10}$ are each independently of the other $C_1$–$C_8$alkyl; or

$X_1$ and $X_2$ are each independently of the other hydrogen; $C_1$–$C_5$alkyl; or $X_1$ and $X_2$, together with the linking nitrogen atom, are an unsubstituted or $C_1$–$C_4$alkyl-substituted pyrrolidino or piperidino ring; and $X_3$ is hydrogen or methyl.

Very particularly preferred are compounds of formula (1), wherein $R_1$ is hydrogen or methyl;

$R_2$ is nitro; $SO_2R_4$; $SO_2OR_5$; $SO_2NR_6R_7$; $COR_8$; $CONR_6R_7$; or $C_1$–$C_4$haloalkyl;

n is 0, 1, 2, 3 or 4;

$R_3$ if n=1, 2, 3 or 4, is halogen; if n=1 or 2, is methyl; or if n=1, is nitro, amino, mono-$C_1$–$C_4$alkylamino or di-$C_1$–$C_4$alkylamino;

$R_4$ is $C_1$–$C_4$alkyl; $C_1$–$C_4$haloalkyl; phenyl which is unsubstituted or substituted by halogen, $C_1$–$C_4$alkyl, or $C_1$–$C_4$alkoxy;

$R_5$ is hydrogen; $C_1$–$C_4$alkyl; $C_1$–$C_4$haloalkyl; phenyl or phenyl-$C_1$–$C_2$alkyl, each unsubstituted or substituted in the phenyl moiety by halogen, $C_1$–$C_4$alkyl, $C_1$–$C_4$haloalkyl or $C_1$–$C_4$alkoxy;

$R_6$ and $R_7$ are each independently of the other hydrogen; or $C_1$–$C_4$alkyl;

$R_8$ is hydrogen; $C_1$–$C_4$alkyl; $C_1$–$C_4$alkoxy; unsubstituted phenyl or phenyl which is substituted by halogen, $C_1$–$C_4$alkyl, $C_1$–$C_4$haloalkyl or $C_1$–$C_4$alkoxy; phenyl-$C_1$–$C_2$alkyl or phenyl-$C_1$–$C_2$alkoxy;

$R_9$ and $R_{10}$ are each independently of the other $C_1$–$C_5$alkyl; or

$X_1$ and $X_2$ are each independently of the other hydrogen; $C_1$–$C_5$alkyl; or $X_1$ and $X_2$, together with the linking nitrogen atom, are an unsubstituted pyrrolidino or piperidino ring; and $X_3$ is hydrogen or methyl.

Important colour formers of formula (1) are those compounds in which $R_2$ is $COR_8$, and $R_8$ is hydrogen; $C_1$–$C_4$alkyl; $C_1$–$C_4$alkoxy; unsubstituted phenyl or phenyl which is substituted by halogen, $C_1$–$C_4$alkyl, $C_1$–$C_4$haloalkyl or $C_1$–$C_4$alkoxy; phenyl-$C_1$–$C_2$alkyl or phenyl-$C_1$–$C_2$alkoxy, and in particular those compounds of formula (1), wherein $R_8$ is $C_1$–$C_4$alkyl, $C_1$–$C_4$alkoxy or phenyl-$C_1$–$C_2$alkoxy.

Preferred colour formers of formula (2) are those compounds in which R10 is $C_1$–$C_8$alkyl.

Colour formers of formula (3) meriting particular interest are those compounds wherein $X_4$ and $X_5$ are each independently of the other unsubstituted phenyl or phenyl which is substituted by halogen, nitro, $C_1$–$C_4$alkyl, $C_1$–$C_4$alkoxy, $C_1$–$C_4$haloalkyl or —$NR_{12}R_{13}$ $Y_3$ is unsubstituted phenyl or phenyl which is substituted by halogen, $C_1$–$C_4$alkyl, $C_1$–$C_4$haloalkyl or $C_1$–$C_4$alkoxy; and the benzene ring A is substituted by halogen; $C_1$–$C_5$alkyl; $C_1$–$C_5$alkoxy; or $NR_{13}R_{14}$.

Preferred colour formers of component (b) are those compounds of formula (4), wherein $Y_1$ and $Y_2$ are each independently of the other $C_3$–$C_5$alkyl and $R_9$ is $C_1$–$C_5$alkyl or $$-\underset{\underset{H}{|}}{C}=O,$$

and $R_{11}$ is hydrogen or $C_1$–$C_5$alkyl;

and, in particular, those compounds wherein $Y_1$ and $Y_2$ are each independently of the other $C_4$–$C_5$alkyl.

Compounds wherein $Y_1$ and $Y_2$ have the same meaning are very particularly preferred.

A particularly preferred colour former mixture comprises as component (a) a compound of formula (1), wherein $R_1$ is hydrogen, halogen or methyl;

$R_2$ is $COR_8$;

n is 0, 1, 2, 3 or 4;

$R_3$ if n=1, 2, 3 or 4, is halogen; if n=1 or 2, is methyl; or if n=1, is nitro, amino, mono-$C_1$–$C_4$alkylamino or di-$C_1$–$C_4$alkylamino;

$R_8$ is hydrogen; $C_1$–$C_4$alkyl; $C_1$–$C_4$alkoxy; unsubstituted phenyl or phenyl substituted by halogen, $C_1$–$C_4$alkyl, $C_1$–$C_4$haloalkyl or $C_1$–$C_4$alkoxy; phenyl-$C_1$–$C_2$-alkyl or phenyl-$C_1$–$C_2$alkoxy;

$X_1$ and $X_2$ are each independently of the other hydrogen; $C_1$–$C_5$alkyl; or $X_1$ and $X_2$, together with the linking nitrogen atom, are an unsubstituted pyrrolidino or piperidino ring; and $X_3$ is hydrogen or methyl;

and/or a compound of formula (2), wherein $R_{10}$ is $C_1$–$C_5$alkyl;

and, as component (b), a compound of formula (4), wherein $Y_1$ and $Y_2$ are $C_3$–$C_5$alkyl, and $R_9$ is $C_1$–$C_5$alkyl; or $$-\underset{\underset{H}{|}}{C}=O,$$

and $R_{11}$ is hydrogen or $C_1$–$C_5$alkyl.

The compounds of formula (1) are disclosed in EP-A-0 561 738 and can be prepared according to the methods described therein.

The compounds of formula (3) and the preparation thereof are disclosed in U.S. Pat. No. 4,675,497.

Some of the compounds of formula (4) are disclosed in, inter alia, U.S. Pat. No. 5,071,480. Some of the compounds of formula (4) are novel. These novel compounds are also an object of the invention.

These novel compounds correspond to formula (4')

wherein

X' is $C_1$–$C_5$alkyl; or $$-\underset{\underset{H}{|}}{C}=O;$$

Y' is $C_4$–$C_5$alkyl; and

R'$_{11}$ is hydrogen or $C_1$–$C_5$alkyl.

The compounds of formula (4') can be prepared by methods known per se, for example by condensing a benzophenone of formula (I)

with a phenol or a phenol ether of formula (II)

in the temperature range from preferably 0° to 70° C. in 50 to 100% sulfuric acid, with removal of the formyl protective group, to a phthalide of formula (III)

and then cyclising said compound of formula (III) in the temperature range from 20° to 100° C. to a compound of formula (4'). In the above formulae (I), (II) and (III), X', Y' and R'$_{11}$ are as defined for formula (4') and R' is hydrogen or $C_1$–$C_4$alkyl.

This process is also an object of the present invention.

The novel colour former mixture can be prepared by simple mixing and milling of said components (a) and (b). Homogeneous powder mixtures are thus obtained which are storage stable at room temperature. The individual colour former components are preferably milled individually in the wet state and then mixed as a dispersion.

The components (a) and (b) are preferably used in crystalline form.

The colour former components (a) and (b) are usually in a weight ratio from 1:5 to 1:1 and preferably from 1:3 to 1:2. The desired colour shades can thus be adjusted.

The colour former mixture of this invention is very well suited to the preparation of pressure-sensitive and in particular of heat-sensitive recording systems. To this end, the components (a) and (b) can also be used separately.

The colour former mixture of this invention is usually colourless or at most faintly coloured. When the sublimation-fast colour former mixtures are brought into contact preferably with an acid developer, i.e. an electron acceptor, they produce deep grey or black images. The colour former mixtures of this invention are also very useful in admixture with one or more than one other known colour formers, typically 3,3-bis(aminophenyl)phthalides such as CVL, 3-indolyl-3-aminophenylaza- or -diazaphthalides, (3,3-bisindolyl)phthalides, 3-aminofluorans, substituted 3,7-diaminofluorans, leukoauramines, spiropyranes, spirodipyranes, chromenopyrazoles, chromenoindoles, phenoxazines, phenothiazines, carbazolyl methanes or other triarylmethaneleuko dyes.

The colour former mixture of this invention exhibits an excellent colour intensity and lightfastness on activated clays as well as on phenolic substrates. It is particularly suitable for use as rapidly developing colour former mixture in a pressure-sensitive or, preferably, in a heat-sensitive recording material which may be a copying material as well as a recording material. The colour former mixture of this invention is storage stable. Compared with the images obtained with a single component such as 2-phenylamino-3-methyl-6-diethylaminofluoran, the black images obtained with the colour former mixture of this invention with phenols exhibit an enhanced storage stability as well as slighter background discoloration.

A pressure-sensitive material typically comprises at least one pair of sheets that contain one colour former mixture of components (a) and (b) dissolved in an organic solvent, and an electron acceptor as developer.

Typical examples of such developers are active clays such as attapulgite clay, acid clay, bentonite, montmorillonite, activated clay such as acid-activated bentonite or montmorillonite, and also zeolite, halloysite, silica, alumina, aluminium sulfate, aluminium phosphate, zinc chloride, zinc nitrate, zirconium dioxide, activated kaolin or any clay. As developers it is also possible to use acidic organic compounds such as ring-substituted phenols, resorcinols, salicylic acids, including 3,5-bis(α,α-dimethylbenzyl)salicylic acid or 3,5-bis(α-methylbenzyl)salicylic acid or salicylates and their metal salts, e.g. zinc salts, as well as an acidic polymeric material such as a phenolic polymer, an alkyl phenol acetylene resin, a maleic acid rosin resin or a partially or completely hydrolysed polymer of maleic anhydride with styrene, ethylene or vinyl methyl ether, or carboxymethylene. Mixtures of the cited monomers and polymers can also be used. Particularly preferred developers are acid-activated bentonite, zinc salicylates or the condensates of p-substituted phenols with formaldehyde. These last mentioned compounds may also be modified with zinc. Zinc salicylates are disclosed, inter alia, in EP-A-181 283 or DE-A-2 242 250.

The developers may also be used in admixture with other basically inert or substantially inert pigments or with other auxiliaries such as silica gel or UV absorbers, e.g. 2-(2'-hydroxyphenyl)benzotriazoles. Examples of such pigments are: talcum, titanium dioxide, alumina, aluminium hydroxide, zinc oxide, chalk, clays such as kaolin, as well as organic pigments, e.g. urea/formaldehyde condensates (BET surface area: 2–75 $m^2/g$) or melamine/formaldehyde condensates.

The colour former mixture produces a coloured image at those points where it comes into contact with the electron acceptor. To prevent the colour formers contained in the pressure-sensitive recording material from becoming active prematurely, they are usually separated from the electron acceptor. This separation can conveniently be accomplished by incorporating the colour formers in foam-like, sponge-like or honeycomb-like structures. The colour formers are preferably encapsulated in microcapsules, which can normally be ruptured by pressure.

When the capsules are ruptured by pressure, for example with a pencil, the colour former solution is transferred to an adjacent sheet which is coated with an electron acceptor and a coloured image is thus produced. The colour results from the dye which is formed and which is absorbed in the visible range of the electromagnetic spectrum.

The colour former mixture is encapsulated preferably in the form of solutions in organic solvents. Examples of suitable solvents are preferably non-volatile solvents, for example a halogenated paraffin, benzene or diphenyl, for example chloroparaffin, trichlorobenzene, monochlorodiphenyl, dichlorodiphenyl or trichlorodiphenyl, and also esters such as tricresyl phosphate, di-n-butyl phthalate, dioctyl phthalate, trichloroethylphosphate, an aromatic ether such as benzylphenyl ether, a hydrocarbon oil such as paraffin or kerosene, aromatic hydrocarbons, an alkylated derivative (e.g. comprising isopropyl, isobutyl, sec- or tert-butyl groups) of diphenyl, naphthalene or terphenyl; dibenzyl toluene, partially hydrogenated terphenyl, mono- to tetra-$C_1$–$C_3$alkylated diphenylalkanes, dodecylbenzene, benzylated xylenes, phenyl xylyl ethane or other chlorinated or hydrogenated condensed aromatic hydrocarbons. Mixtures of different solvents, especially mixtures of paraffin oils or kerosene and diisopropylnaphthalene or partially hydrogenated terphenyl, are often used to obtain optimum solubility of the colour formers, a rapid and intense coloration, and a viscosity which is advantageous for the microencapsulation.

The capsule walls can be formed evenly around the droplets of the colour former solution by coacervation. The encapsulating material is described e.g. in U.S. Pat. No. 2,800,457. The capsules may also be conveniently formed from an aminoplast or a modified aminoplast by polycondensation, as described in British patent specifications 989 264, 1 156 725, 1 301 052 and 1 355 124. Microcapsules which are formed by interfacial polymerisation are also suitable, e.g. capsules formed from polyester, polycarbonate, polysulfonamide, polysulfonate, but preferably from polyamide or polyurethane.

The microcapsules containing the colour former mixture can be used for the production of a wide variety of known kinds of pressure-sensitive copying material. The various systems differ substantially from one another in the arrangement of the capsules, of the colour reactants, and of the support. A preferred arrangement is that in which the encapsulated colour former mixture is in the form of a layer on the back of a transfer sheet and the electron acceptor is in the form of a layer on the face of a receiver sheet.

Another arrangement of the components is that wherein the microcapsules which contain the colour former mixture, and the developer, are in or on the same sheet in the form of one or more individual layers, or the developer is incorporated in the support.

The capsules are preferably secured to the support by means of a suitable binder. As paper is the preferred support, these binders are principally paper-coating agents such as gum arabic, polyvinyl alcohol, hydroxymethyl cellulose, casein, methyl cellulose, dextrin, starch or starch derivatives or polymer latices. These latter are typically butadiene/styrene copolymers or acrylic homopolymers or copolymers.

The paper employed comprises not only normal paper made from cellulose fibres, but also paper in which the cellulose fibres are replaced (partially or completely) by synthetic polymer fibres. The support may also be a plastic sheet.

The colour former mixture of this invention may particularly be used in a thermoreactive recording material. Components (a) and (b) of the novel mixture then develop colour at the same temperature, preferably at 110° to 200° C. The thermoreactive recording material usually comprises at least one layer support, the colour former mixture, an electron acceptor and optionally also a binder and/or wax. If desired, activators or sensitisers may also be present in the recording material.

Thermoreactive recording systems comprise, for example, heat-sensitive recording or copying materials and papers. These systems are used e.g. for recording information, for example in electronic computers, teleprinters or telewriters, or in recording and measuring instruments, e.g. electrocardiographs. The image formation (marking) can also be effected manually with a heated pen. Laser beams can also be used to produce heat-induced images.

The composition of the thermoreactive recording material may be such that the colour former is dispersed or dissolved in one binder layer and the developer is dissolved or dispersed in the binder in a second layer. Another possibility comprises dispersing both the colour former and the developer in one layer. By means of heat the layer or layers are softened at specific areas and the desired colour develops at once at those areas where heat is applied.

Suitable developers are the same electron acceptors as are used in pressure-sensitive papers. Examples of developers are the clays and phenolic resins already mentioned, or also the phenolic compounds disclosed e.g. in German Offenlegungsschrift 1 251 348, for example 4-tert-butylphenol, 4-phenylphenol, methylene bis(p-phenylphenol), 4-hydroxydiphenyl ether, α-naphthol, β-naphthol, methyl or benzyl 4-hydroxybenzoate, 4-hydroxydiphenylsulfone, 4-hydroxy-4'-methyldiphenylsulfone, 4'-hydroxy-4-isopropoxydiphenylsulfone, 4,4'-cyclohexylidenediphenol, 4,4'-isopropylidenediphenol, 4,4'-isopropylidene-bis(2-methylphenol), an antipyrine complex of zinc thiocyanate, a pyridine complex of zinc thiocyanate, 4,4'-bis (hydroxyphenyl)valeric acid, hydroquinone, pyrogallol, phloroglucinol, p-, m- and o-hydroxybenzoic acid, hydroxyphthalic acid, gallic acid, 1-hydroxy-2-naphthoic acid, as well as boric acid or organic, preferably aliphatic, dicarboxylic acids, for example tartaric acid, oxalic acid, maleic acid, citric acid, citraconic acid or succinic acid.

Fusible, film-forming binders may also be used for making the thermoreactive recording material. These binders are usually water-soluble, whereas the colour formers and the developer are sparingly soluble or insoluble in water. The binder should be able to disperse and fix the colour former and the developer at room temperature.

When heated, the mixture comprising the coreactand, aktivator and colour former yysoftens or melts, so that the colour former mixture comes in contact with the developer and a colour is able to form.

Aktivators used in the present colour former mixture are dimethyl terephthalate, benzylbenzyloxybenzoate, dibenzyl terephthalate, phenyl-1-hydroxy-2-naphthoate, p-benzylbiphenyl, 2,6-di-tert-butyl-p-cresol, phenyl salicylate, benzophenone, N-phenylbenzenesulfonamide, phenyl-1-hydroxy-2-naphthoate or 4'4-dibutoxydiphenylsulfone. The activators are preferably auseful for reduction of the melting point of the colour former mixture.

If the colour former mixture and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose and polyvinyl carbazole. The preferred arrangement, however, is that in which the colour former mixture and the developer are contained in one layer in a water-soluble binder.

To ensure the stability of the heat-sensitive recording material or the density of the developed image, the material may be provided with an additional protective layer. Such a protective layer will normally consist of water-soluble and/or water-insoluble resins which are conventional polymeric materials or aqueous emulsions of these polymeric materials.

The thermoreactive layers and resin coatings may comprise further auxiliaries. To improve the degree of whiteness, to facilitate the printing of papers, and to prevent the heated pen from sticking, these layers may comprise e.g. talcum, titanium dioxide, zinc oxide, aluminium hydroxide, calcium carbonate (e.g. chalk), clays or also organic pigments, for example urea/formaldehyde polymers. To effect the colour formation only within a limited temperature range it is possible to add substances such as urea, thiourea, diphenyl thiourea, acetamide, acetanilide, benzene sulfanilide, stearamide, bis(stearoyl)ethylenediamide, phthalic anhydride, metal stearates such as zinc stearate, phthalonitrile, dimethyl terephthalate, dibenzyl terephthalate or other appropriate fusible products which induce the simultaneous melting of the colour former and the developer. Thermographic recording materials preferably comprise waxes, e.g. carnauba wax, montan wax, paraffin wax, polyethylene wax, condensates of higher fatty acid amides and formaldehyde, or condensates of higher fatty acids and ethylenediamine.

Pressure-sensitive and particularly heat-sensitive recording materials of this invention have excellent storage ability and superior paper whiteness (background).

In the following working and application Examples percentages are by weight, unless otherwise indicated.

PREPARATION OF THE NOVEL COMPOUNDS

Example 1

55.4 g of 4'-dibutylamino-2-hydroxybenzophenone-2-carboxylic acid are dissolved at 40° C. in 217 g of 98% sulfuric acid. To this solution are added 21 g of N-methyl-p-anisidine at c. 10° C. and the mixture is stirred for 20 hours at 20°–25° C. The resultant reaction solution is charged to a readily stirrable mixture of 700 ml of water, 800 ml of toluene and 455 ml of 10N aqueous sodium hydroxide. The batch is kept for one hour at reflux at c. 83° C. and the aqueous phase is then separated at c. 70° C. The toluene phase is washed with 2×150 ml of water and the toluene is then distilled off under reduced pressure, giving 65.4 g of the crude product of formula

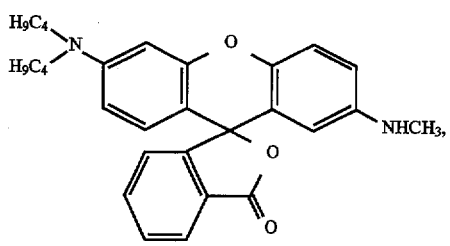

(101)

which, after recrystallisation from a mixture of isopropyl alcohol und toluene, has a melting point of 217°–218° C.

On commercial CF papers as well as in thermoapplication this compound develops an olive-green image on a white background (optical density: 0.008 Db (Db="density black"); measurement is carried out with a GRETAG® SPM100 densitometer; q.v. Example 10).

Example 2

22.2 g of 3'-dibutylamino-2-hydroxybenzophenone-2-carboxylic acid are dissolved at c. 40° C. in 87 g of 98% sulfuric acid. Over 30 minutes, 9.9 g of N-formyl-N-methyl-p-anisidine are added to this solution at c. 10° C. The reaction mass is stirred for 20 hours at 20°–25° C. The formyl protective group is removed by cautiously adding 40 ml of water dropwise and keeping the temperature at c. 100° C. for 1 hour. The resultant solution is then poured into a mixture of 100 ml of water, 400 ml of toluene and 182 ml of 10N aqueous sodium hydroxide (pH=c. 10–11) and kept for 1 hour at reflux. The aqueous phase is separated at 75° C. The toluene phase is washed with 2×200 ml of water at 75° C. and, after removal of the water as an azeotrope, clarified by filtration. The toluene is distilled off and the residue is crystallised in methane, giving 21.9 g of the product of formula (101), which has properties identical to those of this compound.

Examples 3 to 9

The following compounds are prepared (Table 1) in general accordance with the procedure of Example 1:

TABLE 1

| Example | compound of formula | R | $R_2$ | mp [°C.] |
|---|---|---|---|---|
| 3 | (102) | n-butyl | ethyl | 160–162 |
| 4 | (103) | n-butyl | n-butyl | 138–139 |
| 5 | (104) | n-butyl | sec-butyl | 113–114 |
| 6 | (105) | n-butyl | isopropyl | 148–149 |
| 7 | (106) | ethyl | isopropyl | 166–169 |
| 8 | (107) | n-pentyl | methyl | 162–164 |
| 9 | (108) | ethyl | —$CH_2C(CH_3)_3$ | 137–140 |

Example 10a 73.9 g of 3'-dibutylamino-2-hydroxybenzophenone-2-carboxylic acid are dissolved at a maximum temperature of 40° C. in 295 g of 100% sulfuric acid. The solution is cooled to c. 10° C. and 33 g of N-formyl-N-methyl-p-anisidine are added over c. 30 minutes. The reaction mass is stirred for 20 minutes at 20°–25° C. and then poured into 1000 ml of water and 800 g of ice at 0°–10° C.

The suspension is stirred for 1.5 hours, then filtered at 10° C. and the filter product is washed with 400 ml of cold water.

The moist filter cake of formula

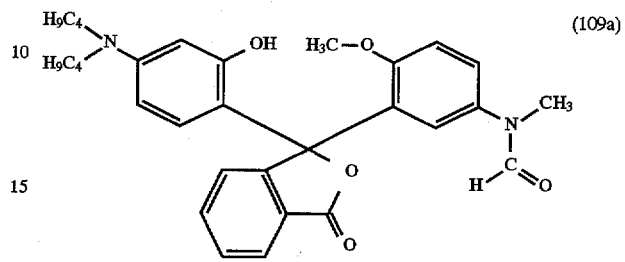

(109a)

is added to a mixture of
- 400 ml of toluene, and
- 100 ml of water, and
- 53 g of sodium carbonate, heated to reflux (c. 81° C.) and kept at this temperature for 7 hours. The toluene phase is separated and washed with water, then dried azeotropically, clarified by filtration with activated carbon and concentrated. The resultant residue weighs 50 g and is recrystallised from isopropyl alcohol, giving colourless crystals of the fluoran of formula

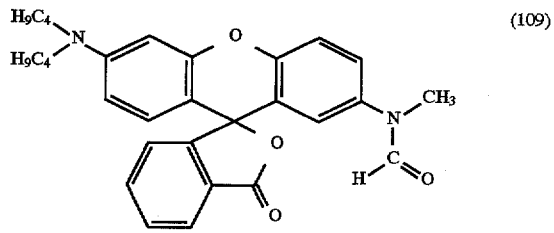

(109)

with a melting point of 193° to 194° C.

Example 10b

The phthalide compound of formula (109a) may also be cyclised to the fluoran of formula (109) by boiling for 2 hours in dimethyl formamide (DMF) at 147°–149° C.

Yield: 95% of theory.

Example 11

20 g of the fluoran of formula (101) are added to 50 ml of technical grade 85% formic acid and heated to reflux temperature (c. 97° C.). After 20 minutes the formylation reaction is complete and the resultant red solution is poured into 1 liter of ice-water at c. 10° C. The batch is allowed to warm to 20°–25° C. and then filtered. The filter product is washed on a suction filter and dried under vacuum at 70° C., giving 18.5 g of a pale pink product of formula (109) with a melting point of 192° to 194° C.

This compound develops a deep red image on commercial CF papers.

In thermoapplication a red image is obtained on a white background (Dm=0.07; Dm="density magenta") likewise. Storage testing of this thermal paper gives excellent results: Dm=0.08 is measured after 1 hour at 58° C. and 50% relative humidity. Dm=1.23 is obtained, with a facsimile machine.

APPLICATION EXAMPLES

Example 12

Use in Thermography a) Preparation of dispersion (A):

1.3 g of the olive colour former of formula (101), and 0.7 g of the orange colour former of formula

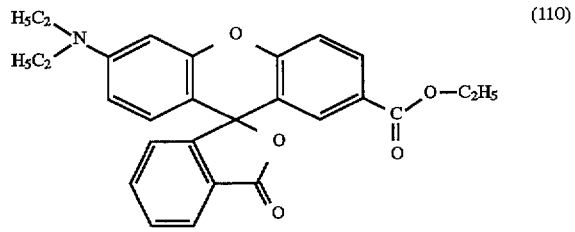
(110)

are milled at room temperature in a ball mill with 7 g of an aqueous 10% solution of polyvinyl alcohol and 4 g of water to a particle size of 1–4 µm.

b) Preparation of dispersion (B):

2 g of 4,4'-isopropylidene diphenol (bisphenol A) are milled at room temperature with 7 g of an aqueous 10% solution of polyvinyl alcohol V03/140 and 4 g of water to a particle size of 2 to 4 µm.

3 parts by weight of dispersion (B) and 1 part by weight of dispersion (A) are mixed thoroughly and then coated on a paper with a coating knife to give a dry coating weight of c. 0.6 g/m² after drying in the air. The paper is kept for 24 hours at 23° C. and 56% relative humidity.

Background colour: 0.06 Db (measurement of the Db value is carded out with a densitometer GRETAG® SPM 100 densitometer).

Black writing with an optical densitiy of Db 1.10 is produced with a commercially available facsimile machine (INFOTEC® 6510).

The dried paper is stored for 1 hour at 58° C. and 50% relative humidity to give a Db value of 0.10.

Example 13

The procedure of Example 12 is repeated except that the colour former components (a) and (b) are milled at first individually and subsequently mixed. The results obtained in Example 12 can thus even be surpassed.

Example 14

1.5 g of the colour former of formula (101) are milled at room temperature in a ball mill with 5.25 g of an aqueous 10% solution of polyvinyl alcohol and 3 g of water to a particle size of 1–4 µm.

0.5 g of tahe compound of formula (111) was milled at room temperature in a second ball mill with 1.75 g of an aqueous 10% solution of polyvinyl alcohol and 1 g of water to a particle size of 1–4 µm.

The colour formers so obtained are then mixed (=dispersion 14A).

3 parts by weight of dispersion B of Example 12 are added to 1 part by weight of dispersion (14A) and the mixture is stirred thoroughly. As described in Example 12, this mixture is coated on a paper and dried. When using a facsimile machine, black writing with an optical density of 1.15 Db develops. The background is white and has an optical density of 0.07 Db.

Example 15

The procedure of Example 12, is repeated but using 0.7 g of 3-cyclohexyl-amino-6-chlorofluoran instead of the orange colour former of formula (110) for the preparation of dispersion (A). When using a facsimile machine, black writing on a white background is obtained.

Example 16

Example 12 is repeated, but using a mixture of colour formers of 1.8 parts by weight of the colour former of formula (101), 0.9 part by weight of the colour former of formula (110), and 0.3 part by weight of the colour former of formula

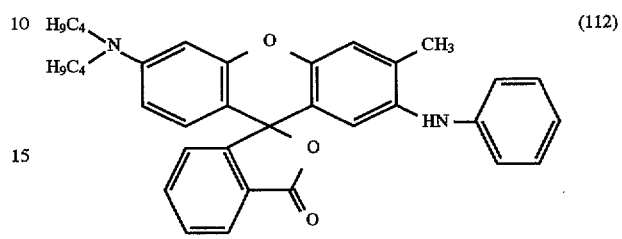
(112)

for the preparation of dispersion (A). When using a facsimile machine, black writing on a white background is obtained.

Example 17

The procedure of Example 12 is repeated, but using a mixture of colour formers of 1.8 parts by weight of the colour former of formula (101), 0.9 part by weight of the colour former of formula (110), and 0.3 part by weight of the colour former of formula

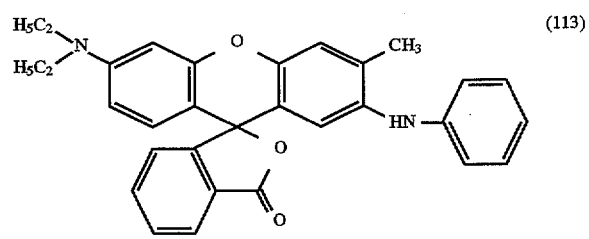
(113)

for the preparation of dispersion (A). When using a facsimile machine, black writing on a white background is obtained.

Example 18

The procedure of Example 12 is repeated, but using a mixture of colour formers of 1.8 parts by weight of the colour formers of formula (101), 0.9 part by weight of the colour former of formula (110), and 0.3 part by weight of the colour former of formula

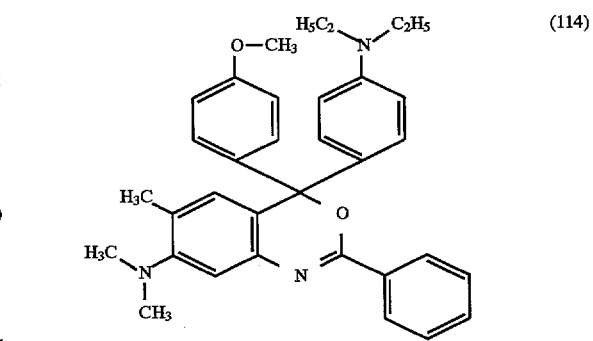
(114)

for the preparation of dispersion (A). When using a facsimile machine, black writing on a white background is obtained.

Example 19

Instead of dispersion (B) of Example 12, the following basic formulation consisting of the following components may be used:

| | Conc. [%] | Solids [g] |
|---|---|---|
| co-reactant bisphenol A or 2,2,-bis-4-hydroxy-4-methylpentane* | 33.3 | 7.5 |
| benzylbiphenyl activator | 25 | 8 |
| MgCO$_3$* | 25 | 6.8 |
| potato starch | 12 | 16.7 |
| zinc stearate* | 20 | 2.5 |
| titanium dioxide* | 25 | 1.6 |
| whitener of the sulfonated stilbene type | 25 | 0.6 |
| carboxylated styrene-butadiene copolymer | 50 | 2 |
| deionised water | 100 | 33.14 |

This basic formulation is prepared as follows: The starred single components are dispersed with a commercial surfactant. Deionised water is then added to this dispersion and the remaining components are subsequently added.

Example 20

Instead of the activators, pigments and co-reactants of Example 20, basic formulations containing the following single compounds are used:

pigments: CaCO$_3$; urea/formaldehyde condensate coreactant: 2,4-dihydroxybenzophenone;

activators: dimethyl terephthalate; benzylbenzyloxybenzoate; dibenzyl terephthalate; phenyl-1-oxy-2-naphthoate; p-benzylbiphenyl; 2,6-di-tert-butyl-p-cresol; phenyl salicylate; benzophenone; N-phenylbenzenesulfonamides; phenyl-1-hydroxy-2-naphthoates; 4'4-dibutoxydiphenylsulfone.

Example 21

Application to copying systems

A solution of 2.2 g of the compound of formula (103), 1.4 g of the compound of formula (110), 0.6 g of 3,3-bis(4-dimethylaminophenyl)-6-dimethylaminophthalide and 0.8 g of N-butylcarbazole-3-yl-bis(4-N-methyl-N-phenylaminophenyl)methane in 80 g of diisopropylnaphthalene and 19 g of kerosene is encapsulated by coacervation by per se known method with gelatine and gum arabic, mixed with a solution of starch and then coated on a sheet of paper. The face of a second sheet of paper is coated with activated clay as colour developer. The first sheet containing the sublimation-fast colour former and the sheet coated with the colour developer are laid on top of each other with their coated sides face to face. Pressure is then exerted onto the first sheet by handwriting or by typewriter and a deep black copy of excellent lightfastness develops immediately on the sheet coated with the developer.

What is claimed is:

1. A colour former mixture, comprising (a) a compound of formula

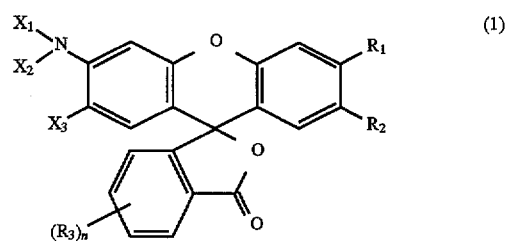

and (b) a compound of formula

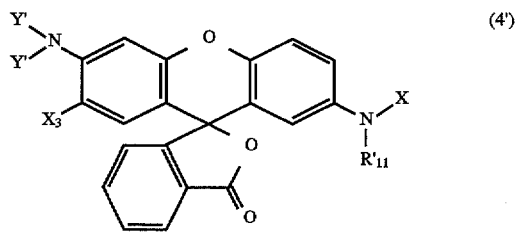

wherein $R_1$ is hydrogen, hydroxy, halogen or $C_1$–$C_4$alkyl;

$R_2$ is hydrogen; nitro; $SO_2R_4$; $SO_2OR_5$; $SO_2NR_6R_7$; $COR_8$; $CONR_6R_7$; or $C_1$–$C_4$haloalkyl; phenylamino; phenyl-$C_1$–$C_4$-alkylamino; an unsubstituted or halogen- or hydroxy-substituted 2-triazinyl or 1-benzotriazolyl radical;

$R_3$ is halogen; nitro; $C_1$–$C_4$alkyl; $C_1$–$C_4$haloalkyl; amino; mono-$C_1$–$C_4$alkylamino; di-$C_1$–$C_4$alkylamino; or $COR_8$;

$R_4$ is $C_1$–$C_8$alkyl; $C_1$–$C_8$haloalkyl; phenyl or phenyl-$C_1$–$C_4$alkyl, each unsubstituted or substituted in the phenyl moiety by halogen, $C_1$–$C_4$alkyl, $C_1$–$C_4$haloalkyl or $C_1$–$C_4$alkoxy;

$R_5$ is hydrogen; $C_1$–$C_8$alkyl; $C_1$–$C_8$haloalkyl; phenyl or phenyl-$C_1$–$C_4$alkyl, each unsubstituted or substituted in the phenyl moiety by halogen, $C_1$–$C_4$alkyl, $C_1$–$C_4$haloalkyl or $C_1$–$C_4$alkoxy;

$R_6$ and $R_7$ are each independently of the other hydrogen or $C_1$–$C_8$alkyl; or $R_6$ and $R_7$, together with the linking nitrogen atom, are an unsubstituted or $C_1$–$C_4$alkyl-substituted pyrrolidino, piperidino, morpholino, thiomorpholino or piperazino ring;

$R_8$ is hydrogen; hydroxy; $C_1$–$C_8$alkyl; $C_1$–$C_8$alkoxy; $C_1$–$C_8$haloalkyl; phenyl which is unsubstituted or substituted by halogen, $C_1$–$C_4$alkyl, $C_1$–$C_4$haloalkyl or $C_1$–$C_4$alkoxy; phenyl-$C_1$–$C_4$alkyl or phenyl-$C_1$–$C_4$alkoxy;

$X_1$ and $X_2$ are each independently of the other hydrogen; $C_1$–$C_8$akyl; $C_4$–$C_7$cycloalkyl which is unsubstituted or substituted by $C_1$–$C_4$alkyl or halogen; unsubstituted phenyl or phenyl which is substituted by $C_1$–$C_4$alkyl, hydroxy or halogen; phenyl-$C_1$–$C_4$alkyl; $C_3$–$C_6$alkenyl; $C_1$–$C_4$alkoxy; $C_1$–$C_4$alkoxy-$C_1$–$C_4$alkyl; 2-tetrahydrofuranyl, or $X_1$ and $X_2$, together with the linking nitrogen atom, are an unsubstituted or $C_1$–$C_4$alkyl-substituted pyrrolidino, piperidino, morpholino, thiomorpholino or piperazino ring;

X' is $C_1$–$C_5$alkyl; or —(CO)H;

Y' is $C_4$–$C_5$alkyl;

$R_{11}$ is hydrogen or $C_1$–$C_5$alkyl; and n is 0; 1; 2; 3; or 4.

2. A colour former mixture according to claim 1, wherein in formula (1)

$R_1$ is hydrogen, halogen or $C_1$–$C_4$alkyl;

$R_2$ is nitro; $SO_2R_4$; $SO_2OR_5$; $SO_2NR_6R_7$; $COR_8$; $CONR_6R_7$; or $C_1$–$C_4$haloalkyl;

n is 0, 1, 2, 3 or 4;

$R_3$ if n=1, 2, 3 or 4, is halogen; if n=1 or 2, is $C_1$–$C_4$alkyl or $C_1$–$C_4$haloalkyl; or if n=1, is nitro, $COR_8$, amino, mono-$C_1$–$C_4$alkylamino or di-$C_1$–$C_4$alkylamino;

$R_4$ i $C_1$–$C_4$alkyl; $C_1$–$C_4$haloalkyl; phenyl or phenyl-$C_1$–$C_2$alkyl, each unsubstituted or substituted in the phenyl moiety by halogen, $C_1$–$C_4$alkyl, $C_1$–$C_4$haloalkyl or $C_1$–$C_4$alkoxy;

$R_5$ is hydrogen; $C_1$–$C_4$alkyl; $C_1$–$C_4$haloalkyl; phenyl or phenyl-$C_1$–$C_2$alkyl, each unsubstituted or substituted in the phenyl moiety by halogen, $C_1$–$C_4$alkyl, $C_1$–$C_4$haloalkyl or $C_1$–$C_4$alkoxy;

$R_6$ and $R_7$ are each independently of the other hydrogen; or $C_1$–$C_4$-alkyl; or $R_6$ and $R_7$, together with the linking nitrogen atom, are an unsubstituted or $C_1$–$C_4$alkyl-substituted pyrrolidino or piperidino ring;

$R_8$ is hydrogen; $C_1$–$C_4$alkyl; $C_1$–$C_4$haloalkyl; $C_1$–$C_4$alkoxy; unsubstituted phenyl or phenyl which is substituted by halogen, $C_1$–$C_4$alkyl, $C_1$–$C_4$haloalkyl or $C_1$–$C_4$alkoxy; phenyl-$C_1$–$C_2$alkyl or phenyl-$C_1$–$C_2$alkoxy;

$R_9$ and $R_{10}$ are each independently of the other $C_1$–$C_8$alkyl; or

$X_1$ and $X_2$ are each independently of the other hydrogen; $C_1$–$C_5$-alkyl; or $X_1$ and $X_2$, together with the linking nitrogen atom, are an unsubstituted or $C_1$–$C_4$alkyl-substituted pyrrolidino or piperidino ring; and $X_3$ is hydrogen or methyl.

3. A colour former mixture according to claim 1, wherein in formula (1)

$R_1$ is hydrogen or methyl;

$R_2$ is nitro; $SO_2R_4$; $SO_2OR_5$; $SO_2NR_6R_7$; $COR_8$; $CONR_6R_7$; or $C_1$–$C_4$haloalkyl;

n is 0, 1, 2, 3 or 4;

$R_3$ if n=1, 2, 3 or 4, is halogen; if n=1 or 2, is methyl; or if n=1, is nitro, amino, mono-$C_1$–$C_4$-alkylamino or di-$C_1$–$C_4$alkylamino;

$R_4$ is $C_1$–$C_4$alkyl; $C_1$–$C_4$haloalkyl; unsubstituted phenyl or phenyl which is substituted by halogen, $C_1$–$C_4$alkyl or $C_1$–$C_4$alkoxy;

$R_5$ is hydrogen; $C_1$–$C_4$alkyl; $C_1$–$C_4$haloalkyl; phenyl or phenyl-$C_1$–$C_2$alkyl, each unsubstituted or substituted in the phenyl moiety by halogen, $C_1$–$C_4$alkyl, $C_1$–$C_4$haloalkyl or $C_1$–$C_4$alkoxy;

$R_6$ and $R_7$ are each independently of the other hydrogen; or $C_1$–$C_4$alkyl;

$R_8$ is hydrogen; $C_1$–$C_4$alkyl; unsubstituted phenyl or phenyl which is substituted by halogen, $C_1$–$C_4$alkyl, $C_1$–$C_4$haloalkyl or $C_1$–$C_4$alkoxy; phenyl-$C_1$–$C_2$alkyl or phenyl-$C_1$–$C_2$alkoxy;

$R_9$ and $R_{10}$ are each independently of the other $C_1$–$C_8$alkyl; or

$X_1$ and $X_2$ are each independently of the other hydrogen; $C_1$–$C_5$alkyl; or $X_1$ and $X_2$, together with the linking nitrogen atom, are an unsubstituted pyrrolidino or piperidino ring; and $X_3$ is hydrogen or methyl.

4. A colour former mixture according to claim 1, comprising a colour former of formula (1), wherein $R_2$ is $COR_8$, $R_8$ is hydrogen; $C_1$–$C_4$alkyl; $C_1$–$C_4$alkoxy; unsubstituted phenyl or phenyl which is substituted by halogen, $C_1$–$C_4$alkyl, $C_1$–$C_4$haloalkyl or $C_1$–$C_4$alkoxy; phenyl-$C_1$–$C_2$alkyl or phenyl-$C_1$–$C_2$alkoxy, $R_2$ is $COR_8$ and $R_8$ is hydrogen; $C_1$–$C_4$alkyl; $C_1$–$C_4$alkoxy; phenyl which is unsubstituted or substituted by halogen, $C_1$–$C_4$alkyl, $C_1$–$C_4$haloalkyl or $C_1$–$C_4$alkoxy; phenyl-$C_1$–$C_2$alkyl or phenyl-$C_1$–$C_2$alkoxy.

5. A colour former mixture according to claim 1, wherein the weight ratio of (a):(b) is 1:5 to 1:1.

6. A colour former mixture according to claim 1, wherein components (a) and (b) are in crystalline form.

7. A pressure-sensitive recording material comprising a support material containing a colour former mixture according to claim 1.

8. A heat-sensitive colour former material comprising a support material containing a colour former mixture according to claim 1.

9. A heat-sensitive recording material according to claim 8, consisting of a heat-sensitive layer comprising the colour former mixture and a developer for the colour former mixture.

10. A colour former mixture according to claim 1, wherein, in formula (1), $R_2$ is hydrogen; nitro; $SO_2R_4$; $SO_2OR_5$; $SO_2NR_6R_7$; $COR_8$; $CONR_6R_7$; $C_1$–$C_4$haloalkyl; or an unsubstituted or halogen- or hydroxy-substituted 2-triazinyl or 1-benzotriazolyl radical.

11. A microencapsulated solution comprising a colour former mixture according to claim 1.

* * * * *

UNITED STATES PATENT AND TRADEMARK OFFICE
CERTIFICATE OF CORRECTION

PATENT NO. : 5,681,791

DATED: : OCTOBER 28, 1997

INVENTOR(S) : ZINK ET AL

It is certified that errors appear in the above-identified patent and that said Letters Patent is hereby corrected as shown below:

Column 18, line 15, delete formula (4') and substitute with:

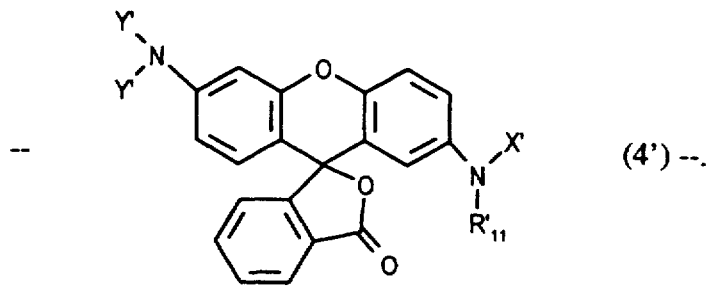

-- (4') --.

Column 18, between lines 65 and 66, please insert:

-- $X_3$ is hydrogen or $C_1$-$C_4$alkyl; --.

Column 19, line 1, delete "$R_{11}$ is hydrogen or $C_1$-$C_5$alkyl; and" and substitute with:

-- $R'_{11}$ is hydrogen or $C_1$-$C_5$alkyl; and --.

UNITED STATES PATENT AND TRADEMARK OFFICE
CERTIFICATE OF CORRECTION

PATENT NO. : 5,681,791
DATED : OCTOBER 28, 1997
INVENTOR(S) : ZINK ET AL

It is certified that error appears in the above-indentified patent and that said Letters Patent is hereby corrected as shown below:

Column 19, line 13, delete "$R_4$ i $C_1$-$C_4$alkyl; $C_1$-$C_4$haloalkyl; phenyl or phenyl-" and substitute with:

-- $R_4$ is $C_1$-$C_4$alkyl; $C_1$-$C_4$haloalkyl; phenyl or phenyl- --.

Signed and Sealed this

Thirtieth Day of June, 1998

Attest:

BRUCE LEHMAN

Attesting Officer

Commissioner of Patents and Trademarks